Jan. 24, 1961 S. F. MOLFINO Plant Pat. 2,014

PEACH TREE

Filed Nov. 27, 1959

WITNESS

Addison E. Avery

INVENTOR

Samuel F. Molfino

Webster & Webster

ATTYS.

United States Patent Office

Plant Pat. 2,014
Patented Jan. 24, 1961

2,014

PEACH TREE

Samuel F. Molfino, Strathmore, Calif., assignor to Kenneth R. Clifford, Strathmore, Calif.

Filed Nov. 27, 1959, Ser. No. 855,952

1 Claim. (Cl. 47—62)

This discovery relates to a new and distinct variety of peach tree which originated as a seedling of the Heath clingstone peach (unpatented). The present variety, while retaining the general characteristics of the Heath—including the flavor and aroma of the fruit—is distinct in that such fruit is wholly freestone; thus providing an excellent marketable peach primarily for dessert use, but also having medium shipping quality.

The variety was discovered by me under the following circumstances:

A number of seeds from the Heath clingstone peach were discarded in the yard of the residence on my ranch located near Strathmore, California, and several of such seeds sprouted and produced seedlings. One of such seedlings appeared to be especially healthy and vigorous, and I therefore permitted it to develop to maturity under conditions which were subject to my control, continued observation, irrigation, and cultivation. When such seedling grew to maturity and came into bearing I recognized the distinctive freestone nature of the fruit as compared to the Heath clingstone peach.

It is believed that the instant variety originated by cross-pollination of the Heath clingstone peach with an unknown nectarine; this for the reason that the fruit produced by the present variety occasionally has a smooth skin characteristic of a nectarine, and most seeds produce nectarine seedlings.

After I recognized the variety as being new and distinct I asexually reproduced it, on my ranch located as aforesaid, by budding; such reproductions—under careful observation, and when they reached maturity and came into bearing—having run true to the parent tree in all respects.

Figure 1:
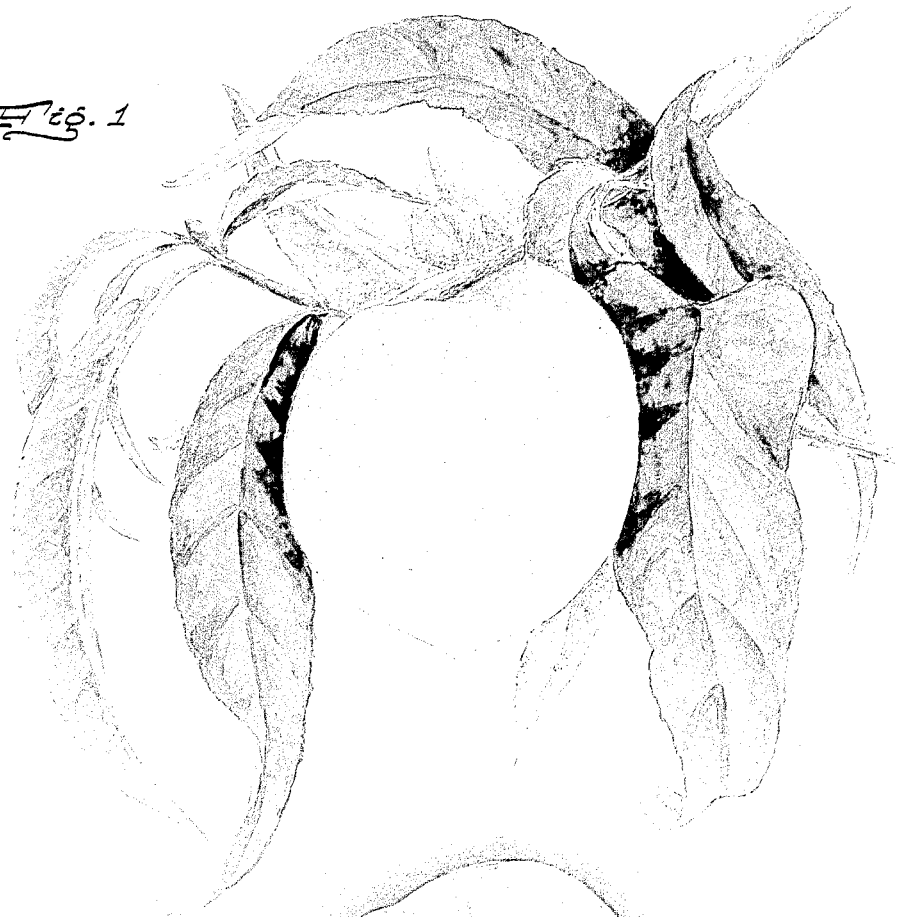
Fig. 1 is an elevation of one of the fruit, together with a twig and leaves.
Figure 2:
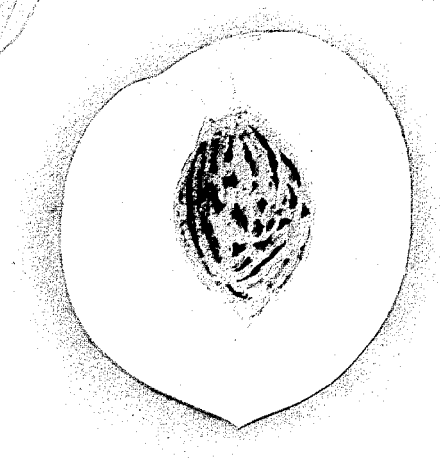
Fig. 2 is a sectional elevation of one of the fruit, with the stone exposed.

Referring now to the pomological details of this new and distinct variety of peach tree and its fruit, the following is an outline description thereof; all major color plate identifications—except where terms of common definition are employed—being by reference to Maerz and Paul Dictionary of Color:

Tree:
- *Size.*—Large.
- *Vigor.*—Vigorous.
- *Growth.*—Upright.
- *Density.*—Dense.
- *Form.*—Vase shaped.
- *Hardiness.*—Hardy.
- *Production.*—Very productive.
- *Bearing.*—Regular bearer.

Trunk:
- *Size.*—Medium.
- *Texture.*—Medium.

Branches:
- *Size.*—Medium.
- *Texture.*—Medium.
- *Color.*—Dull grey.
- *Lenticels.*—Medium number; medium size.

Leaves:
- *Size.*—Large. Average length—6". Average width—1½".
- *Form.*—Ovate; acuminate; acutely pointed.
- *Thickness.*—Medium.
- *Texture.*—Smooth.
- *Color.*—Top side—medium green (22–L–8). Under side—lighter green (21–I–7).
- *Margin.*—Crenate; finely serrate.
- *Petiole.*—Medium length; thick.
- *Glands.*—Average number—three. Alternate; medium size; reniform; green. Position—base of blade.
- *Stipules.*—None.

Flower Buds:
- *Hardiness.*—Hardy.
- *Size.*—Large.
- *Length.*—Medium.
- *Form.*—Plump; appressed.
- *Pubescence.*—None.

Flowers:
- *Blooming period.*—Medium as compared with other varieties.
- *Size.*—Large.
- *Color.*—Pink.

Fruit:
- *Average date of first picking.*—August 10th.
- *Average date of last picking.*—August 26th.
- *Size.*—Uniform; medium. Average diameter axially—2⅞". Average transversely in suture plane—3".
- *Form.*—Uniform; symmetrical; globose; compressed laterally.
- *Suture.*—Distinct; shallow. Extends from base to beyond—but discontinuous at—apex, with slight depression beyond pistil point.
- *Ventral surface.*—Rounded slightly; lipped toward base, both sides; lips equal.
- *Cavity.*—Circular; elongated in suture plane, with suture showing on one side. Average depth—¼" to ⅜". Average breadth—⅝".
- *Base.*—Rounded.
- *Apex.*—Short.
- *Pistil point.*—Apical.

Skin:
- *Thickness.*—Medium.
- *Toughness.*—Medium.
- *Tenacity to flesh.*—Free.
- *Tendency to crack.*—Slight.
- *Down.*—Scant; short; does not roll up when rubbed. Occasional fruit has a nectarine-like smooth skin.
- *Color.*—Light yellow with greenish cast (9–F–1 to 10–G–5), partially blushed with red (4–J–9 to 4–L–10).

Flesh:
- *Amygdalin.*—Wanting.
- *Juice.*—Moderate.
- *Texture.*—Medium; melting.
- *Fibers.*—Few.
- *Ripens.*—Even.
- *Flavor.*—Subacid, delicate.
- *Aroma.*—Pronounced.
- *Eating quality.*—Best.
- *Color.*—Cream (9–C–2 to 9–H–3), streaked and mottled with red (1–H–7 to 1–K–9) next to stone. Surface of pit cavity—red with white fibers.

Stone:

*Type.*—Free.

*Size.*—Medium. Average length—1½". Average breadth—15/16. Average thickness—⅝".

*Form.*—Oval; cuneate.

*Base.*—Straight.

*Hilum.*—Oval.

*Apex.*—Acuminate.

*Sides.*—Equal; curved on right and left.

*Surface.*—Regularly furrowed near base; pitted from base to above center.

*Ridges.*—Rounded toward base; interrupted.

*Pits.*—Elongated.

*Ventral edge.*—Thick, without wing toward base.

*Dorsal edge.*—Full, with shallow narrow groove to above center.

*Tendency to split.*—Slight.

*Color.*—Brown (7-H-11 to 8-L-12).

Use: Market; dessert.

Keeping quality: Medium.

Shipping Quality: Medium.

The tree and its fruit herein described may vary in slight detail due to climatic and soil conditions under which the variety may be grown; the present description being of the variety as grown in the Central Valley of California.

The following is claimed:

A new and distinct variety of peach tree, as illustrated and described, having general resemblance in tree and fruit to the Heath clingstone peach but distinctively characterized in comparison by freestone fruit; and further characterized by fruit which normally has scant short down but occasionally is nectarine-smooth.

No references cited.